(12) United States Patent  
Nakabayashi (10) Patent No.: US 9,033,881 B2  
(45) Date of Patent: May 19, 2015

(54) OBJECT INFORMATION ACQUISITION APPARATUS

(71) Applicant: CANON KABUSHIKI KAISHA, Tokyo (JP)

(72) Inventor: Takaaki Nakabayashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/706,191

(22) Filed: Dec. 5, 2012

(65) Prior Publication Data

US 2013/0165795 A1  Jun. 27, 2013

(30) Foreign Application Priority Data

Dec. 21, 2011  (JP) ................................. 2011-279727

(51) Int. Cl.
 *A61B 8/00*  (2006.01)
 *A61B 8/08*  (2006.01)
 *A61B 5/00*  (2006.01)

(52) U.S. Cl.
 CPC .............. *A61B 8/0825* (2013.01); *A61B 8/406* (2013.01); *A61B 8/4209* (2013.01); *A61B 5/0095* (2013.01)

(58) Field of Classification Search
 USPC .................... 600/407, 437, 441, 443
 See application file for complete search history.

(56) References Cited

U.S. PATENT DOCUMENTS

| 7,229,411 | B2 * | 6/2007 | Slayton et al. | ................ 600/439 |
| 7,744,534 | B2 * | 6/2010 | Chalana et al. | ............... 600/437 |
| 2003/0018255 | A1 * | 1/2003 | Martin et al. | ................. 600/437 |
| 2013/0225970 | A1 * | 8/2013 | Nakabayashi | ................ 600/407 |

FOREIGN PATENT DOCUMENTS

| JP | 2010-167004 A | 8/2010 |
| JP | 2011-103913 A | 6/2011 |
| JP | 2011-229620 A | 11/2011 |

* cited by examiner

*Primary Examiner* — Unsu Jung  
*Assistant Examiner* — Joel Lamprecht  
(74) *Attorney, Agent, or Firm* — Canon USA, Inc., IP Division (57) ABSTRACT

An object information acquisition apparatus includes a holding member, a probe unit, a transducer, a housing, an opposing member, and a separating member. The holding member holds an object. The probe unit scans with respect to the holding member and includes a housing and a transducer positioned to form a space between the transducer and the holding member. The transducer receives an acoustic wave from the object through the holding member and is housed in the housing. The opposing member is provided at an upper position relative to an area that is scannable with the probe unit. The separating member is provided in at least one of the probe unit and the opposing member and having a shape that is changeable. The separating member reduces spreading of a matching liquid that has flowed onto the housing from the space between the transducer and the holding member.

22 Claims, 7 Drawing Sheets

OBJECT INFORMATION ACQUISITION APPARATUS

BACKGROUND OF THE INVENTION

1. Field of the Invention

The present invention relates to an object information acquisition apparatus that receives an acoustic wave from an object to be tested.

2. Description of the Related Art

As an object information acquisition apparatus that receives acoustic waves to acquire object information, Japanese Patent Laid-Open No. 2011-103913 discloses an apparatus utilizing the photo-acoustic effect. With this apparatus, an acoustic wave generated in an object as a result of illumination of light is received by a probe and converted into an image. In this apparatus, two opposing holding members hold a breast as the object, and when receiving an acoustic wave, two-dimensional scanning is performed in the horizontal and vertical directions along the holding members using the probe. A housing, in which the probe (transducer) is housed, is provided with an oil seal to allow a space between the probe and the holding member to be filled with a matching liquid such as oil that is used to match the acoustic impedance. The oil seal has an opening formed on its upper surface in order to remove bubbles entrained in the matching liquid. The matching liquid having overflowed from the opening flows downward along the holding member and is recovered in a tank using a recovery mechanism.

Although the above-described document discloses that the matching liquid having overflowed flows downward along the holding member, there is no consideration for a case in which the matching liquid overflows onto the upper surface of the housing (that is, a case in which the matching liquid stays on the upper surface of the housing).

SUMMARY OF THE INVENTION

Figure 1:
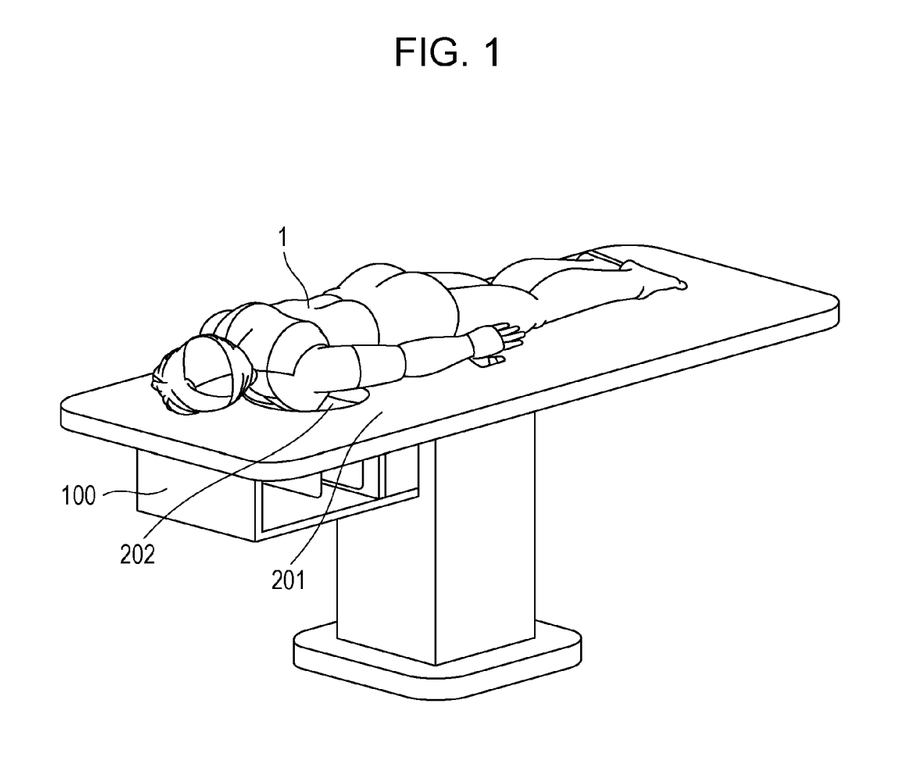
FIG. 1 is a perspective view generally illustrating an object information acquisition apparatus.

As illustrated in FIG. 1, in an apparatus in which a subject lies face-down on a bed (supporting member 201) and the breast inserted through an opening 202 is held by a holding member, the bed is positioned on the vertically upper side relative to a probe. There may also be a reinforcing member provided at a vertically upper position relative to the probe. The reinforcing member suppresses deformation of the holding member when an object is held by the holding member.

The inventor studied a case in which the probe was moved upward while a matching liquid overflowed onto the upper surface of a housing. As a result of the study, it has been found that the matching liquid may spread and contaminate the interior of the apparatus through contact of the matching liquid with the bed, the reinforcing member, and the like provided at upper positions relative to the housing. In order to avoid occurrence of such a situation, it is thought to limit upward scanning such that scanning in areas closest to the bed or the reinforcing member is not performed, thereby avoiding contact of the matching liquid with the bed, the reinforcing member, or the like. However, in the case where the upward scanning is limited, a dead space in which object information cannot be acquired is formed.

In view of the above-described problem, the embodiments provide an object information acquisition apparatus with which spreading of the matching liquid is reduced without increasing the dead space.

To address the above-described problem, an embodiment adopts the following structure. That is, according to an aspect of the present invention, an object information acquisition apparatus includes a holding member configured to hold an object, a probe unit configured to scan with respect to the holding member, the probe unit including a transducer positioned to form a space between the transducer and the holding member and configured to receive an acoustic wave from the object through the holding member, and a housing configured to house the transducer, an opposing member provided at an upper position relative to an area that is scannable with the probe unit, and a separating member provided in at least one of the probe unit and the opposing member and having a shape that is changeable, in which the separating member is configured to reduce spreading of a matching liquid that has flowed onto the housing from the space between the transducer and the holding member.

According to the embodiments, spreading of the matching liquid can be reduced.

Further features of the present invention will become apparent from the following description of exemplary embodiments with reference to the attached drawings.

DESCRIPTION OF THE EMBODIMENTS

The following is focused: a matching liquid spreads and contaminates the interior of an apparatus through contact of the matching liquid with opposing members such as a bed and a reinforcing member provided at upper positions relative to the housing. In particular, a cable, in which wiring that connects an electric signal output from a probe to a processing unit such as a computer is gathered, is provided on the rear of a probe unit (a space on a side opposite to a holding member with respect to the probe unit) that includes the probe. Thus, when the matching liquid spreads rearward, the matching liquid not only contaminates the interior of the apparatus but also adheres to the cable, and in some cases, the matching liquid enters a portion in which the probe unit and the cable are connected to each other. There also is a case in which the matching liquid, having spread rearward, cannot be recovered in an oil tray provided at a lower position relative to a holding member.

Thus, a separating member, the shape of which is changeable, is provided in at least one of the probe unit and the opposing member, thereby reducing spreading of the matching liquid in at least one direction without increasing a dead space. The separating member can reduce spreading of the matching liquid toward the rear of the probe unit.

In the embodiments, examples of an acoustic wave include elastic waves referred to as a sonic wave, an ultrasonic wave, a photoacoustic wave, and a photoultrasonic wave. The probe receives an acoustic wave having propagated through an object. An object information acquisition apparatus according to the embodiments includes a device that emits light (an electromagnetic wave, the examples thereof include visible light and infrared light) to the object to generate an acoustic wave in the object and receives the acoustic wave, thereby acquiring object information.

Object information to be acquired indicates characteristic information, in which an initial sound pressure distribution of an acoustic wave generated when the object is irradiated with light, a light energy absorption density distribution introduced from the initial sound pressure distribution, an absorption coefficient distribution, concentration distributions of substances included in tissue, and the like are reflected. The examples of the concentration distributions of substance include, for example, an oxygen saturation distribution, a distribution of oxidized/reduced hemoglobin concentration, and the like. The object information may be acquired not only as numeric data but also as distribution information at positions in the object. That is, distribution information such as an absorption coefficient distribution and an oxygen saturation distribution may be acquired as image data.

Alternatively, the object information acquisition apparatus may utilize an ultrasonic echo technique, in which the object information is acquired by transmitting an ultrasonic wave to the object and receiving the wave reflected by the object. With the apparatus utilizing the ultrasonic echo technique, the object information to be acquired is characteristic information in which the difference in acoustic impedance among tissues in the object is reflected.

Embodiments will be described below with reference to the drawings. In general, like reference numerals refer to like elements, thereby omitting description thereof.

First Embodiment

In a first embodiment, an example of an apparatus, with which an object is irradiated with light and an acoustic wave generated in the object is received by a probe to acquire information about the object, is described. FIG. 1 is a perspective view generally illustrating an object information acquisition apparatus according to the present embodiment. The object information acquisition apparatus includes a supporting member 201 serving as a bed that supports a subject 1 and a measurement unit 100 provided at a lower position relative to the supporting member 201. The supporting member 201 has an opening 202 into which an object, which is part of the subject 1 such as a human breast, is inserted. A probe unit 10 (FIG. 2), which receives an acoustic wave from the object, is provided in the measurement unit 100.

Measurement Unit

Figure 2:
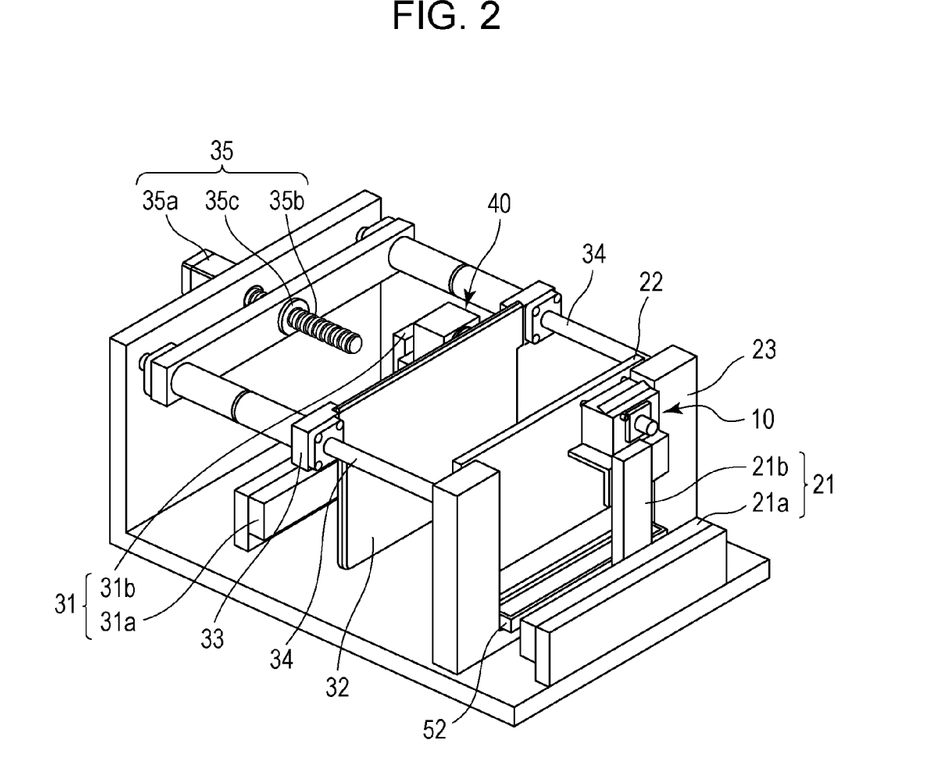
FIG. 2 is a perspective view generally illustrating a measurement unit.

FIG. 2 is a perspective view of the measurement unit 100. The measurement unit 100 at least includes the probe unit 10, an optical unit 40, a fixed holding member 22, and a movable holding member 32. The fixed holding member 22 and the movable holding member 32 are holding members. An oil tray 52 is provided at a lower position relative to the fixed holding member 22. The oil tray 52 recovers matching oil that has overflowed from a space formed between a probe 11 (FIG. 3A) in the probe unit 10 and the fixed holding member 22. The oil tray 52 is disposed to receive the matching oil falling along the fixed holding member 22.

The probe unit 10 is attached to a probe scanning unit 21, which includes two axis units, that is, a horizontal axis unit 21a and a vertical axis unit 21b. Thus, the probe unit 10 is capable of scanning in a two-dimensional direction along the fixed holding member 22. The probe scanning unit 21 is controlled by a computer or a microcontroller (not shown). In the present embodiment, the supporting member 201 is provided at an upper position relative to the probe unit 10. That is, in the present embodiment, an opposing member provided at an upper position relative to an area scannable by the probe unit 10 is the supporting member 201. However, the opposing member is not limited to the supporting member 201. The opposing member includes members provided at upper positions relative to the area scannable by the probe such as a reinforcing member that reinforces the holding member. In the embodiments, the term "downward (or down or lower)" refers to a direction in which the gravity acts (direction of the gravitational field), and the term "upward (or up or upper)" refers to a direction opposite to the direction in which the gravity acts. Although the embodiments are described in terms of direction/positional relationship, the embodiment structures are not restricted to the described direction/positional relationship.

Holding Member

The fixed holding member 22 and the movable holding member 32 that opposes the fixed holding member 22 hold and compress the object to be measured from the respective sides. The fixed holding member 22 can be formed of resin, polymethylpentene in particular, to match the acoustic impedance from the object to the probe 11 (see FIGS. 3A and 3B). The fixed holding member 22 is secured to a fixing plate 23. The movable holding member 32 is secured to a movable plate 33. The movable plate 33 is movable using guide rods 34 in a direction in which the movable plate 33 holds and compresses the object. The movable plate 33 is driven by a holding member drive mechanism 35. The holding member drive mechanism 35 includes a motor 35a, a ball screw 35b, and nut 35c. Since a member in which the nut 35c is provided is connected to the movable plate 33, the movable holding member 32 is moved by driving the motor 35a.

Optical Unit

The optical unit 40 is disposed at a position that opposes the probe unit 10 disposed on the fixed holding member 22 side. Light is introduced to the optical unit 40 from a light source (not shown) through an optical system such as a fiber or a lens. The object is irradiated with the light from an outgoing end of the optical system in the optical unit 40. The light source uses a laser that generates pulsed light of the order of nanoseconds. As is the case with the probe scanning unit 21, an optical scanning unit 31, which includes two axis units, that is, a horizontal axis unit 31a and a vertical axis unit 31b, allows the optical unit 40 to scan in a two-dimensional direction. As is the case with the probe scanning unit 21, the optical scanning unit 31 is controlled by a computer or a microcontroller (not shown). By controlling the probe scanning unit 21 and the optical scanning unit 31 in a synchronized manner, the optical unit 40 and the probe unit 10, which oppose each other with the object interposed therebetween, can perform scanning while being constantly positioned to oppose each other.

In the present embodiment, the probe unit 10 is provided on the fixed holding member 22 side and the optical unit 40 is provided on the movable holding member 32 side. However, the present invention is not limited to the above-described structure. The probe unit 10 may be provided on the movable holding member 32 side or on both the fixed holding member 22 and the movable holding member 32 sides. Likewise, the optical unit 40 may be provided on the fixed holding member 22 side or on both the fixed holding member 22 and the movable holding member 32 sides. Furthermore, a fiber or the like may be inserted into the probe unit 10 to emit the light from the inside of the probe unit 10. The detailed structure of the probe unit 10 is described below.

Probe Unit

Figure 3A:
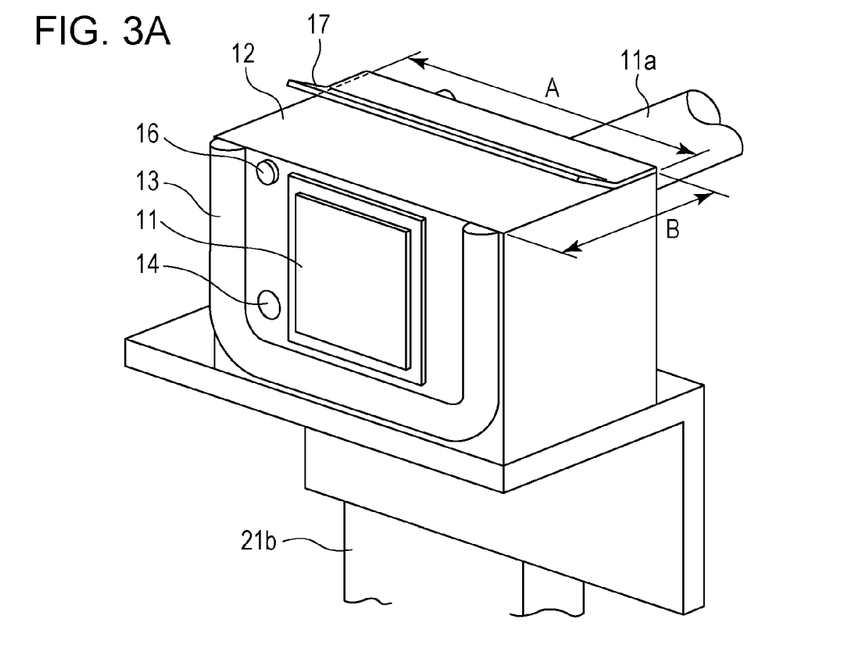
FIGS. 3A and 3B are respectively a perspective view and a top view generally illustrating a probe unit according to a first embodiment.
Figure 3B:
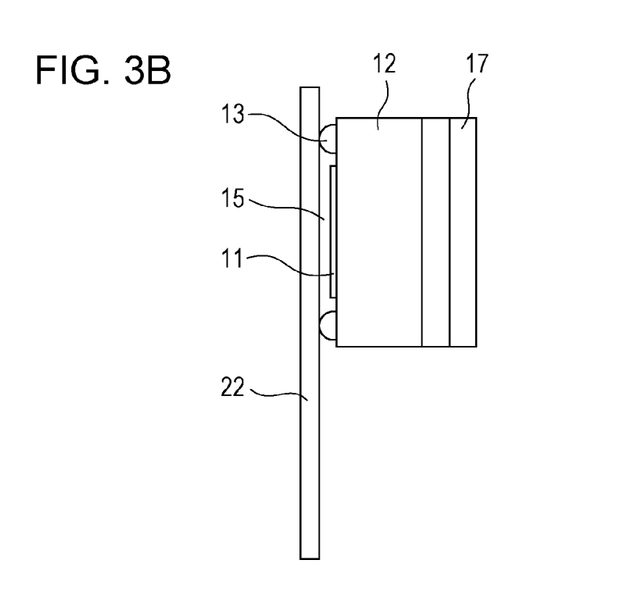

FIGS. 3A and 3B are schematic diagrams of the probe unit 10. FIG. 3A is a perspective view of the probe unit 10 and FIG. 3B is a top view of the probe unit 10. The probe unit 10 includes the probe 11 that receives an acoustic wave from the object through the fixed holding member 22. In the embodiments, the term "probe" refers to a transducer that receives an acoustic wave and converts the received acoustic wave into an electric signal. The probe may use, for example, a transducer such as a piezoelectric element utilizing piezoelectric phenomena, a transducer utilizing optical resonance, a transducer utilizing changes in capacitance, or any other transducer as long as the transducer can receive an acoustic wave and convert the received acoustic wave into an electric signal. The transducer may be a single transducer element, or may include a plurality of transducers arranged in an array.

The probe 11 is housed in and secured to a housing 12. The housing 12 includes a sealing member 13 that surrounds the probe 11. The sealing member 13 may use a packing formed of a material such as rubber, a porous material (sponge), leather, or resin. With the sealing member 13, a space 15 is formed between the fixed holding member 22 and the probe 11. The space 15 holds matching oil, which is a matching liquid used to match the acoustic impedance.

The sealing member 13 has an opening formed in an upper portion thereof to release air entrained in the matching oil. The housing 12 has a supply port 14 formed therein that supplies the matching oil into the space 15 using a pump (not shown). The pump is controlled by a computer or a microcontroller (not shown). The matching liquid can be deaerated. The matching liquid may use water or the like instead of oil.

An oil fence 17, which is formed of a polyethylene terephthalate (PET) film, is provided in an upper portion of the housing 12. The oil fence 17 serves as a separating member. In the embodiment, when the matching liquid contacts the opposing member, such as the supporting member 201, the separating member 17 reduces spreading of the matching liquid that overflows onto the housing 12. In the present embodiment, the separating member 17 reduces spreading of the matching oil rearward with respect to the probe unit 10 (toward a space on a side opposite to the holding member 22 with respect to the probe unit 10). Furthermore, the shape of the separating member 17 is changeable in accordance with stress applied thereto, such as from contact with the supporting member 201, thereby allowing the probe unit 10 to scan to a position very close to the opposing member even when the separating member 17 and the opposing member (or, the separating member 17 and the probe unit 10 as will be described in a second embodiment) are brought into contact with each other.

It should be understood that the dimensions, materials, shapes, and relative arrangement of the components of the separating member that will be described below are to be appropriately changed in accordance with the structure of a device to which the present invention is applied and a variety of conditions, and are not intended to limit the scope of the present invention to the following description.

The oil fence 17 of the present embodiment serving as the separating member is bent in a diagonally upward direction relative to an upper surface of the housing 12 and inclined upwards toward the probe 11 relative to the vertical direction (up-down direction). Thus, when the probe unit 10 is vertically moved and brought into contact with the supporting member 201, a force exerted on the oil fence 17 acts in the direction in which the oil fence 17 is bent. That is, the shape of the oil fence 17 is changeable. The oil fence 17 may be formed of a resin sheet made of a material other than PET, for example, polycarbonate (PC), or may be formed of a material having spring properties such as sheet metal or rubber. A connection portion in which the housing 12 and the oil fence 17 are connected to each other is formed using an adhesive having sealing properties so that the matching oil having flowed onto the upper surface of the housing 12 does not leak therethrough. Alternatively, the housing 12 and the oil fence 17 may be, for example, pressed by a separate member with rubber, a porous material (sponge), or the like pinched therebetween to be connected to each other. The oil fence 17 can be connected to the housing 12 through the entire length of the side A of the housing 12. The above-described structure increases the effect, by which flowing of the matching oil having flowed onto the upper surface of the housing 12 toward a probe cable 11a provided on the rear of the probe 11 is suppressed.

During measurement, in which the probe 11 receives an acoustic wave, the space 15, which is bounded by the fixed holding member 22, the probe 11, and the sealing member 13 (at least between the fixed holding member 22 and the probe 11), should be filled with the matching oil. A liquid level sensor 16 is provided in the housing 12 at an upper position relative to the probe 11. When the liquid level sensor 16 can detect the matching oil, the space 15 between the fixed holding member 22 and the probe 11 is determined to have been filled with the matching oil.

As preparation for measurement, whether or not the space 15 has been filled with the matching oil is checked in accordance with a result of detection performed by the liquid level sensor 16. In the case where the space 15 is determined to have been filled with the matching oil, the preparation for measurement is completed. During measurement, the matching oil continues to be supplied to the space 15 so that an amount of the matching oil sufficient for measurement can be maintained, even when the matching oil leaks due to scanning performed by the probe unit 10.

Scanning Path of Probe Unit 10

Figure 4:
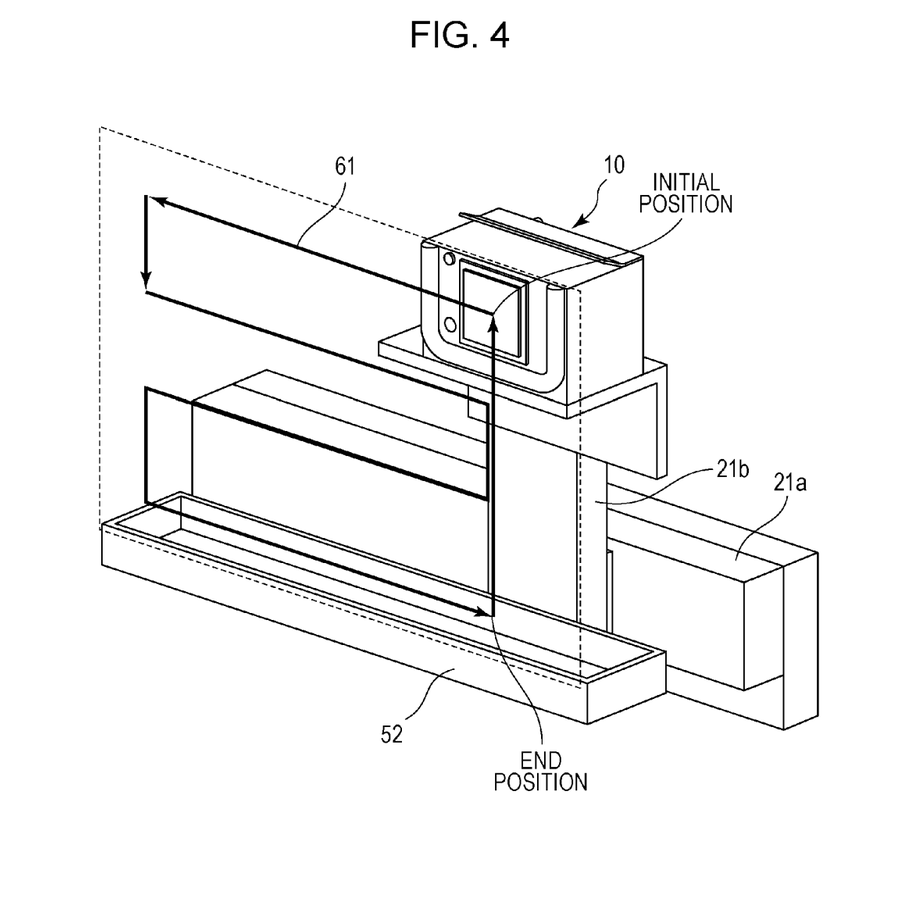
FIG. 4 is a perspective view illustrating a path of the probe unit according to the first embodiment.

Next, a scanning path of the probe unit 10 is described. FIG. 4 is a schematic diagram illustrating a path of the probe unit 10 during measurement. Arrows 61 indicate a path of scanning (movement) performed by the probe unit 10 during measurement.

The probe unit 10 is positioned at an uppermost portion of a measurement area (scanning area) in an initial stage of measurement. When measurement is started, as indicated by the arrows 61, the probe unit 10 continuously scans a line in a horizontal direction, then moved downward by a line and scans the next line in a direction opposite to the previous line while receiving an acoustic wave. This operation is repeated so that scanning is performed line by line from the top. The probe unit 10 having reached an end position returns to an initial position and the measurement is completed. The scanning method is not limited to the above-described method. Alternatively, for example, scanning may be performed upward from a lower position, or scanning may be a step and repeat scanning, in which the probe unit 10 is stopped at each receiving position to receive the acoustic wave. Regarding a technique that converts object information into image data utilizing an electrical signal output from the probe 11 having received an acoustic wave, a related-art method can be used.

Figure 5A:
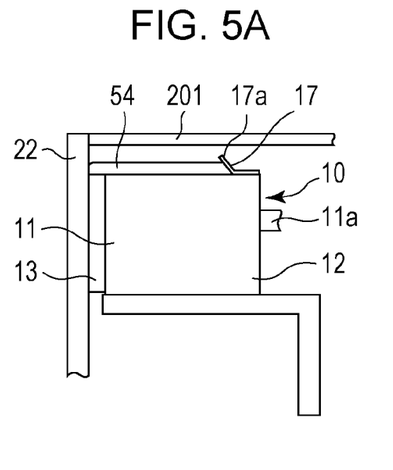
FIGS. 5A to 5D are schematic diagrams illustrating changes in the state of the probe unit in vertical scanning according to the first embodiment.
Figure 5B:
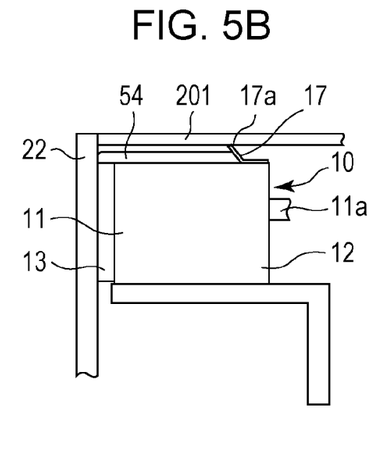
Figure 5C:
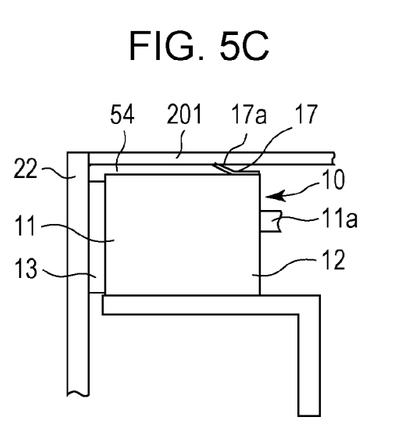
Figure 5D:
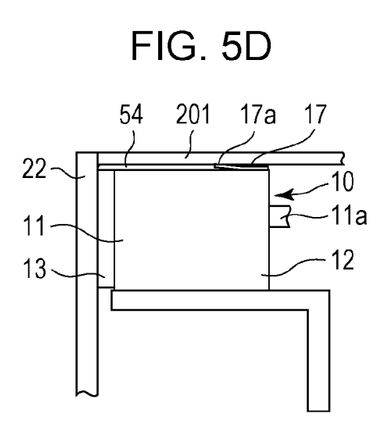

FIGS. 5A to 5D illustrate states of the probe unit 10 when the probe unit 10 is moved from a lower position (for example, the end position) to the uppermost portion (for example, the initial position). FIG. 5A illustrates a state in which the probe unit 10 is positioned at a lower position. FIG. 5B illustrates a state in which the oil fence 17 is brought into contact with the supporting member 201. FIG. 5C illustrates a state in which the matching oil is brought into contact with the supporting member 201. FIG. 5D illustrates a state in which the probe unit 10 has been moved to the uppermost portion.

In FIG. 5A, the matching oil, having overflowed from the space 15 onto the upper surface of the housing 12, remains on the upper surface of the housing 12 until the matching oil forms a layer 54 having a specified thickness (for example, about 3 mm) due to surface tension, and then flows downward. In the present embodiment, since the oil fence 17 is connected to the housing 12 through the entire width of the housing 12, the matching oil flows downward from side surfaces of the housing 12 instead of flowing through sides of the oil fence 17 toward the probe cable 11a. Also in the present embodiment, an end 17a (uppermost portion) of the oil fence 17 is positioned at a level higher than an upper end of the layer 54 of the matching oil when no load is applied to the end 17a of the oil fence 17.

Next, as illustrated in FIG. 5B, the probe unit 10 is moved upward from the lower position to approach the supporting member 201. Here, in order to decrease a region in which object information cannot be acquired by the probe unit 10 (dead space) around the opposing member, the probe unit 10 should be moved to a position immediately close to a height at which the supporting member 201, as the opposing member, is disposed. That is, the probe unit 10 is caused to scan such that the gap between the upper surface of the housing 12 and a lower surface of the supporting member 201 formed when the probe unit 10 is positioned at the uppermost portion is narrower (smaller) than the thickness of the layer 54 of the matching oil. In the present embodiment, the end 17a of the oil fence 17 is positioned at a level higher than the upper end of the layer 54 of the matching oil when no load is applied to the end 17a of the oil fence 17. Thus, when the probe unit 10 is moved upward, the end 17a of the oil fence 17 is initially brought into contact with the supporting member 201, thus, the state illustrated in FIG. 5B is entered. That is, the oil fence 17 is brought into contact with the supporting member 201 earlier than the matching oil is.

When the probe unit 10 is moved further upward, the oil fence 17 is bent and deformed in accordance with the gap between the housing 12 and the supporting member 201 while being in contact with the supporting member 201. The oil fence 17 is bent downward towards the layer 54. After that, the layer 54 of the matching oil is brought into contact with the supporting member 201. Thus, the state illustrated in FIG. 5C is entered. When the probe unit 10 is moved further upward, the layer 54 of the matching oil held between the supporting member 201 and the housing 12 is pushed out of the upper surface of the housing 12 by the bending of the oil fence 17 and narrowing of the space between the supporting member 201 and the oil fence 17. The matching oil flows downward to the side surface sides. At this time, since the oil fence 17 and the supporting member 201 are in contact with each other, spreading of the matching oil toward the probe cable 11a, which is positioned on the opposite side with respect to the oil fence 17, is suppressed (or reduced). Thus, even after the matching oil has been brought into contact with the supporting member 201, spreading of the matching oil toward the probe cable 11a can be reduced while the probe unit 10 can be moved to the uppermost portion as illustrated in FIG. 5D.

Modifications

Figure 6A:
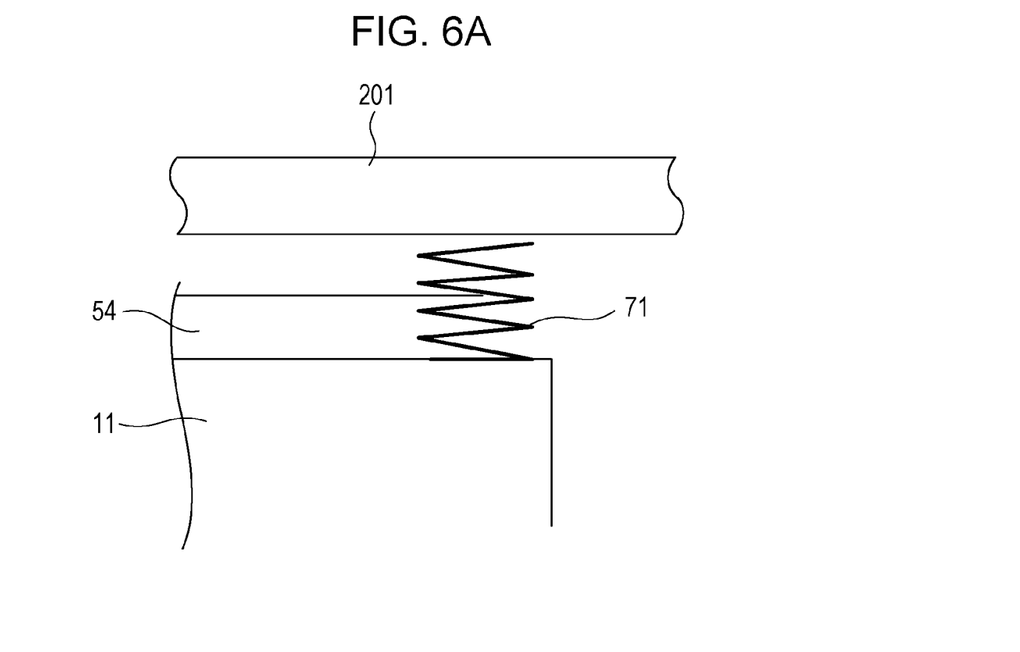
FIGS. 6A and 6B are schematic diagrams illustrating modifications of a separating member according to the first embodiment.
Figure 6B:
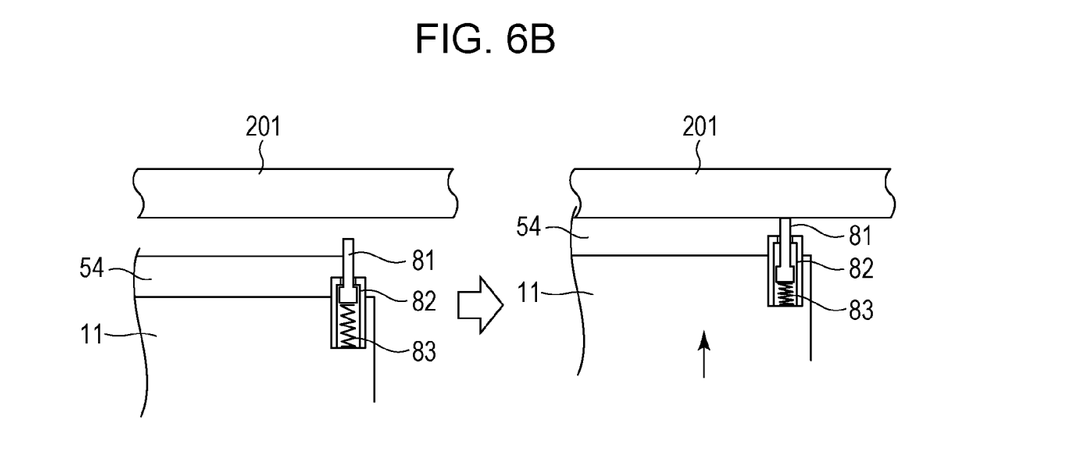

In the above-described example, the oil fence 17, which is flexible in the vertical direction (up-down direction), is brought into contact with the supporting member 201 earlier than the matching oil is. However, the separating member according to the present embodiment is not necessarily formed to have flexibility, and is sufficient when the shape of the entirety of the separating member be changeable. In an example, the oil fence 17 may be resilient and return to an original form or position after being bent, compressed, or stretched. Furthermore, the separating member is not necessarily formed of a single component. The separating member may include two or more components. FIGS. 6A and 6B are schematic diagrams illustrating modifications of the separating member.

FIG. 6A is a schematic diagram illustrating a modification of the separating member formed of a single component. An oil fence 71 has a bellows-like shape, which, as a flexible corrugated element, allows the oil fence 71 to vertically extend or contract. Also with this structure, the oil fence 71 can be brought into contact with the supporting member 201 earlier than the matching oil is and the shape of the oil fence 71 is changeable in accordance with a vertical movement of the probe unit 10.

FIG. 6B illustrates another modification of the oil fence as the separating member formed of two or more components. The oil fence includes a fence unit 81, a slide guide 82, and a spring 83. The slide guide 82 is provided in the housing 12. The fence unit 81 is vertically movable along/within the slide guide 82. The fence unit 81 is urged toward the supporting member 201 by the spring 83. That is, the separating member includes the fence unit 81, the slide guide 82, and the spring 83, so that the shape of the entirety of the separating member is changeable. The fence unit 81 is constantly in contact with the supporting member 201 by the urging force of the spring 83 while being pressed against the supporting member 201 due to the movement of the probe unit 10. The fence unit 81, which can be moved by the spring 83, may be formed of a material having stiffness.

With the previously described structures, the separating member is provided at a position at which the separating member reduces spreading of the matching oil toward the probe cable 11a of the probe unit 10. However, the present invention is not limited to such structures. It is sufficient that spreading of the matching oil toward at least in one direction be reduced. For example, in the case where an electrical circuit and the like are provided in a space on one of the side surface sides of the housing (that is, also the side surface side of the probe unit), the separating member may be provided on the side surface side of the housing 12 illustrated in FIGS. 3A and 3B to reduce spreading of the matching oil toward the side surface. In this case, the separating member can be connected to the housing through the entire length of the side B. Furthermore, in order to reduce spreading of the matching oil toward spaces on both the rear and the side surface side of the probe unit, the separating members may be provided along both the side A and side B.

With the structure according to the present embodiment, when the probe unit 10 is moved upward, spreading of the matching liquid is reduced by the separating member even in the case where the matching liquid having overflowed onto the upper surface of the housing 12 is brought into contact with the opposing member.

Second Embodiment

In a second embodiment, a separating member is provided at a position different from that of the first embodiment.

Figure 7A:
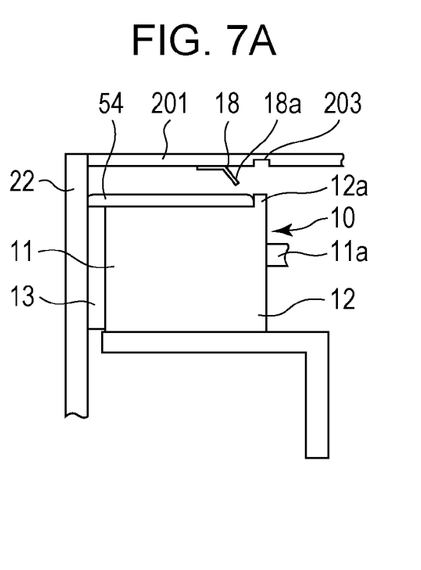
FIGS. 7A to 7D are schematic diagrams illustrating changes in the state of the probe unit in vertical scanning according to a second embodiment.
Figure 7B:
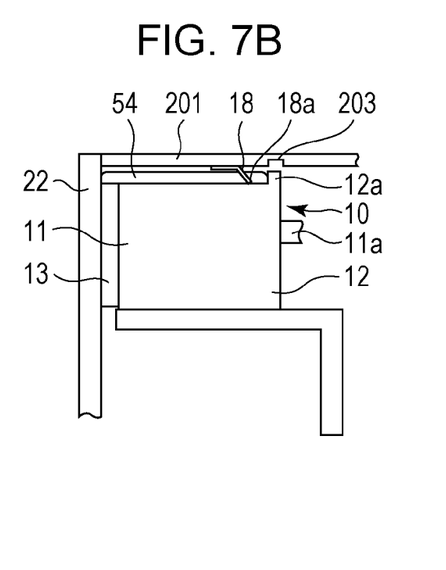
Figure 7C:
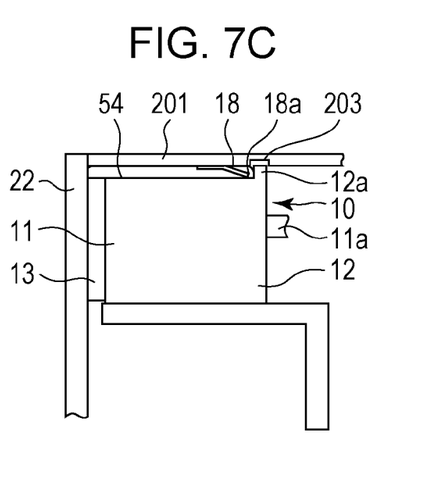
Figure 7D:
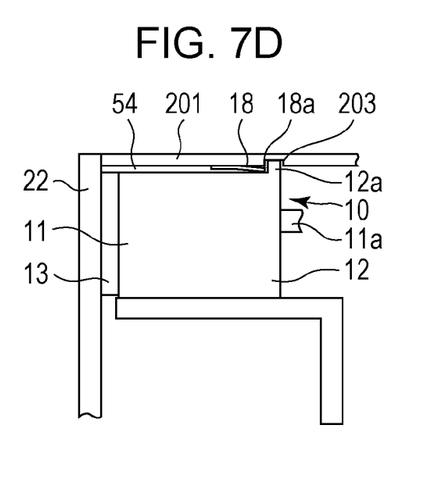

FIGS. 7A to 7D are side views of the probe unit 10 according to the second embodiment, illustrating states of the probe unit 10 when the probe unit 10 is moved from a lower position (for example, the end position) to the uppermost portion (for example, the initial position). FIG. 7A illustrates a state in which the probe unit 10 is positioned at a lower position. FIG. 7B illustrates a state in which an oil fence 18 is brought into contact with the housing 12. FIG. 7C illustrates a state in which the matching oil is brought into contact with the supporting member 201. FIG. 7D illustrates a state in which the probe unit 10 has been moved to the uppermost portion.

In the second embodiment, the oil fence 18 serving as the separating member is provided in the supporting member 201 serving as the opposing member. The oil fence 18 is bent in a diagonally downward direction relative to the supporting member 201 and away from the layer 54. Thus, when the probe unit 10 is vertically moved and brought into contact with the supporting member 201, a force from the supporting member 201 is exerted in a direction in which the oil fence 18 is caused to bend. That is, the shape of the oil fence 18 is changeable. As is the case with the first embodiment, a connecting portion in which the oil fence 18 and the supporting member 201 are connected to each other has sealing properties. The direction of an end 18a of the oil fence 18 may be opposite to the direction illustrated in FIGS. 7A to 7D. That is, the end 18a may be positioned on the probe 11 side (left side on the page of FIGS. 7A to 7D) relative to a contact portion in which the oil fence 18 is in contact with the supporting member 201 such that the oil fence 18 is bent in a diagonally downward direction relative to the supporting member 201 and towards the layer 54.

In the present embodiment, as illustrated in FIG. 7A, an oil fence 12a is formed as the separating member on the supporting member side so that the layer 54 of the matching oil (matching liquid) having overflowed onto the upper surface of the housing 12 does not flow down toward the probe cable 11a. However, the matching liquid spreads in particular when the matching liquid is brought into contact with the opposing member. Thus, it is sufficient in the present embodiment that the separating member be provided at least on the supporting member 201, which is the opposing member, side, and the separating member on the probe unit 10 side is not necessarily provided. That is, it is sufficient that the separating member be provided in at least one of the probe unit 10 and the opposing member 201. Also in the present embodiment, in the case where the oil fence 12a is provided, a groove 203 is formed in the supporting member 201 so that the oil fence 12a does not interfere with the supporting member 201 when the probe unit 10 is moved to the uppermost portion. With this structure, the dead space, in which object information cannot be acquired by the probe unit 10, is decreased.

As illustrated in FIG. 7B, when the probe unit 10 is moved upward, the oil fence 18 is initially brought into contact with the housing 12. This is because the distance between the end 18a of the oil fence 18 and the supporting member 201 is larger than the thickness of the layer 54 of the matching oil. Thus, when the probe unit 10 is moved upward, the oil fence 18 is brought into contact with the housing 12 earlier than the matching oil is brought into contact with the supporting member 201. When the probe unit 10 is moved further upward than the position thereof illustrated in FIG. 7B, the oil fence 18 deforms while being in contact with the housing 12.

After that, the layer 54 of the matching oil is brought into contact with the supporting member 201, and the state illustrated in FIG. 7C is entered. When the probe unit 10 is moved further upward, the layer 54 of the matching oil held between the supporting member 201 and the housing 12 is pushed out of the upper surface of the housing 12 and flows downward on the side surface sides. At this time, since the oil fence 18 and the housing 12 are in contact with each other, spreading of the matching oil toward the probe cable 11a, which is positioned on the opposite side with respect to the oil fence 18, is reduced. Thus, even after the matching oil has been brought into contact with the supporting member 201, spreading of the matching oil toward the probe cable 11a can be reduced while the probe unit 10 can be moved to the uppermost portion as illustrated in FIG. 7D. When the probe unit 10 is positioned in the uppermost portion, here, the end 18a of the oil fence 18 may resided adjacent to the oil fence 12a.

Accordingly, also in the present embodiment, when the matching oil having overflowed onto the upper surface of the housing 12 is brought into contact with the supporting member 201, spreading of the matching oil toward the probe cable 11a is reduced. Also in the present embodiment, the separating members as described in the modifications of the first embodiment (see FIGS. 6A and 6B) may be provided on the opposing member side. As described in the first embodiment, the separating member according to the present embodiment is not limited to a structure with which spreading of the matching oil toward the rear of the probe unit 10 is reduced. The separate member may reduce spreading of the matching oil toward one of the spaces of the side surfaces of the probe unit 10. It is sufficient that the separate member reduce spreading of the matching oil in at least one direction.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-279727, filed Dec. 21, 2011, which is hereby incorporated by reference herein in its entirety.

What is claimed is:

1. An object information acquisition apparatus comprising:
a holding member configured to hold an object;
a probe unit having a transducer and a housing configured to house the transducer, wherein the probe unit is configured to scan with respect to the holding member, the transducer is configured to receive an acoustic wave from the object through the holding member, and the housing includes a housing top, a housing rear, and a front center located between the transducer and the housing rear, wherein the probe unit forms a space between the transducer and the holding member to hold a matching liquid for acoustic matching of the transducer and the holding member, wherein the space is opposed to the holding member so that matching liquid held in the space is movable onto the housing top;
an opposing member provided at an upper position relative to an area that is scannable with the probe unit; and
a separating member positioned on one of the probe unit and the opposing member to reduce spreading of the matching liquid from the housing top,
wherein, in response to the separating member engaging the other one of the probe unit and the opposing member, the separating member changes shape such that the matching liquid adjacent to the separating member moves away from the separating member and towards the front center of the housing.

2. The object information acquisition apparatus according to claim 1, wherein a cable is provided on an opposite side of the probe unit opposite to the holding member and wiring for an electric signal output from the transducer is gathered in the cable.

3. The object information acquisition apparatus according to claim 1, wherein the opposing member is a supporting member configured to support subject that includes the object.

4. The object information acquisition apparatus according to claim 1, wherein the separating member is a member having flexibility.

5. The object information acquisition apparatus according to claim 4, wherein the separating member is resilient in that the separating member returns to an original form or position after being bent, compressed, or stretched.

6. The object information acquisition apparatus according to claim 1, wherein the opposing member is a reinforcing member that reinforces the holding member.

7. An object information acquisition apparatus comprising:
a holding member configured to hold an object;
a probe unit configured to scan with respect to the holding member, the probe unit including a transducer configured to receive an acoustic wave from the object through the holding member, and a housing configured to house the transducer; and
an opposing member provided at an upper position relative to an area that is scannable with the probe unit,
wherein the probe unit forms a space to hold a matching liquid for acoustic matching between the transducer and the holding member and is opposed to the holding member so that the matching liquid held in the space is movable onto the housing, and a separating member is provided in at least one of the probe unit and the opposing member, the separating member having a shape that is changeable and configured to reduce spreading, from the housing, of a matching liquid that has been supplied between the transducer and the holding member and moved onto the housing.

8. An object information acquisition apparatus comprising:
a holding member configured to hold an object;
a probe unit facing to the holding member and comprising
a base member facing to and spaced apart from the holding member and configured to be scanned respect to the holding member,
a matching liquid holder located between the holding member and the base member and connected to the base member so as to form a space to store an acoustic matching liquid within, and
a probe having a transducer receiving an acoustic wave from the object via the acoustic matching liquid stored within the space and connected to the base member;
an opposing member located via a gap in opposition to the probe unit, which is connected to the holding member; and
a deformable member located in the gap,
wherein the deformable member is connected to any one of the probe unit and the opposing member.

9. The object information acquisition apparatus according to claim 8, wherein the deformable member is located between the holding member and a connected portion at which the probe unit and the cable are connected to each other.

10. The object information acquisition apparatus according to claim 9, wherein the deformable member is located between the acoustic matching liquid holder and the connected portion.

11. The object information acquisition apparatus according to claim 9, wherein the connected portion is located at an opposite side of the holding member.

12. The object information acquisition apparatus according to claim 8, wherein the deformable member is connected to any one of the probe unit and the opposing member with an adhesive having a sealing property.

13. The object information acquisition apparatus according to claim 8, wherein the deformable member is unconnected to the other one of the probe unit and the opposing member.

14. The object information acquisition apparatus according to claim 8, wherein the deformable member is resilient in that the deformable member returns to an original form or position after being bent, compressed, or stretched.

15. The object information acquisition apparatus according to claim 8, wherein, in response to the probe unit approaching the opposing member, the flow of the acoustic matching liquid is controlled such that the deformable member is brought into contact with the other of the probe unit and the opposing member before the acoustic matching liquid is brought into contact with the opposing member.

16. The object information acquisition apparatus according to claim 8, wherein the opposing member is a supporting member configured to support subject that includes the object.

17. The object information acquisition apparatus according to claim 8, wherein the opposing member is a part of a bed on which a subject is lying prone.

18. The object information acquisition apparatus according to claim 17, wherein the bed has a through hole which the object is inserted through.

19. The object information acquisition apparatus according to claim 18, wherein the holding member is located underneath the through hole.

20. The object information acquisition apparatus according to claim 18, wherein the object is a human breast of the subject.

21. The object information acquisition apparatus according to claim 8, wherein the space is communicated via an inlet with a pump configured to supply the acoustic matching liquid into.

22. The object information acquisition apparatus according to claim 8, wherein the matching liquid holder has an opening facing to the opposing member.

* * * * *